US005407802A

United States Patent [19]
Eisenbarth et al.

[11] Patent Number: 5,407,802
[45] Date of Patent: Apr. 18, 1995

[54] METHOD OF ACCESSING THE RISKS OF DEVELOPING TYPE I DIABETES

[75] Inventors: George S. Eisenbarth, Wellesley; Roberto Gianani, Boston, both of Mass.

[73] Assignee: Immulogic Pharmaceutical Corporation, Waltham, Mass.

[21] Appl. No.: 814,006

[22] Filed: Dec. 26, 1991

[51] Int. Cl.⁶ .......................................... B01N 33/567
[52] U.S. Cl. ................................... 435/7.21; 435/7.4; 436/506; 436/518; 436/811
[58] Field of Search ................... 435/7.21, 7.4, 1, 960; 436/63, 501, 503, 506, 507, 518, 536, 538, 543, 547, 175, 822, 824, 825, 811; 530/387.1, 388.15, 388.26

[56] References Cited

FOREIGN PATENT DOCUMENTS

WO9007117  6/1990  WIPO .

OTHER PUBLICATIONS

Vardi et al., *Diabetologia*, 34: 93–102 (1991).
Bonifacio, et al., *The Lancet*, 335: 147–149 (Jan. 20, 1990).
Riley, et al., *N. Eng. J. Med.*, 323: 1167–1172 (Oct. 25, 1990).
Colman, P. G. et al., *Diabetes*, 37: 645–652 (May 1988).
Baekkeskov, S. et al., *J. Clin. Invest.*, 79: 926–934 (Mar. 1987).
Gianani, R., et al., *Diabetes* 40 Suppl. 1; 224A. (Jun. 1991).
Ziegler, R., et al., *Horm. Res.* 33: 144–151 (1990).
Eisenbarth, G., *Mount Sinai Journal of Medicine* 58(4): 274–279 (Sep. 4, 1991).
Erlich, H. A., et al., *Diabetes* 40: 478–481 (Apr. 1991).
Ziegler, R., et al., *Diabetes* 40: 709–714 (Jun. 1990).
Kaufman, D. L. et al. (Jan. 1991) Autoimmunity to Two Forms of Glutamate Decarboxylase in Insulin–dependent Diabetes Mellitus J. Clin. Invest. 89: 283–292.
Cram, D. S. et al. (May 1991) Cloning And Partial Nucleotide Sequence Of Human Glutamic Acid Decarboxylase cDNA From Brain And Pancreatic Islets *Biochem Biophys. Res. Comm.* 176(3): 1239–1244.
Michelsen, B. K. et al. (Oct. 1991) Cloning, Characterization, and autoimmune recognition of rat islet glutamic acid decarboxylase in insulin–dependent diabetes mellitus Proc. Natl. Acad. Sci. USA 88:8754–8758.
Kaufman, D. L. et al. (1986) Two Forms of the γAminobutyric Acid Synthetic Enzyme Glutamate Decarboxylase Have Distinct Intraneuronal Distributions and Cofactor Interactions *J. Neurochem.* 56:720–723.
Baermier, H. et al., "Risk for Developing Type 1 Insulin–Dependent, Diabetes Mellitus and the Presence of Islets 64K Antibodies," Abstract and full reference *Diabetologia* 34 (10), 1991, pp. 727–733.
Christgau, S. et al., "Pancreatic B Cells Express Two Autoantigenic Forms of Glutamic Acid Decarboxylase, a 65-kDa Hydrophilic Form and a 64-kDa Amphiphilic Form Which Can Be Both Membrane–bound and soluble", *The Journal of Biological Chemistry*, vol. 266, No. 31, Nov. 5, 1991, pp. 21257–21264.
Ziegler et al. *Diabetes Care* vol. 13 (1990) pp. 762–775.
Ziegler, et al., *Diabetes*, 38: 1320–1325 (1989).

*Primary Examiner*—Esther M. Kepplinger
*Assistant Examiner*—Donna C. Wortman
*Attorney, Agent, or Firm*—Lahive & Cockfield

[57] ABSTRACT

Two subsets of Islet Cell Autoantibodies (ICA), termed restricted and non-restricted, have been identified. The expression of non-restricted ICA correlates with progression to type I diabetes, indicating that these individuals are at much greater risk than are individuals expressing restricted ICA. Differentiation between restricted or non-restricted ICA allows for more accurate prognosis of the development of type I diabetes. Restricted ICA react with beta cells of human and rat islets but not mouse, whereas non-restricted ICA react with humans rat and mouse islets. Restricted ICA can be substantially completely absorbed by incubation with glutamic acid decarboxylase (GAD), whereas non-restricted ICA are partially or not at all absorbed by GAD. Restricted ICA react in a Stiff-Man Syndrome fashion including staining GABAergic neurons in brain sections and western blots of brain extracts, whereas non-restricted ICA does not react with either brain sections nor with GAD antigen in western blots. Restricted ICA contains a higher titer of anti-GAD antibodies than does non-restricted ICA.

7 Claims, 7 Drawing Sheets

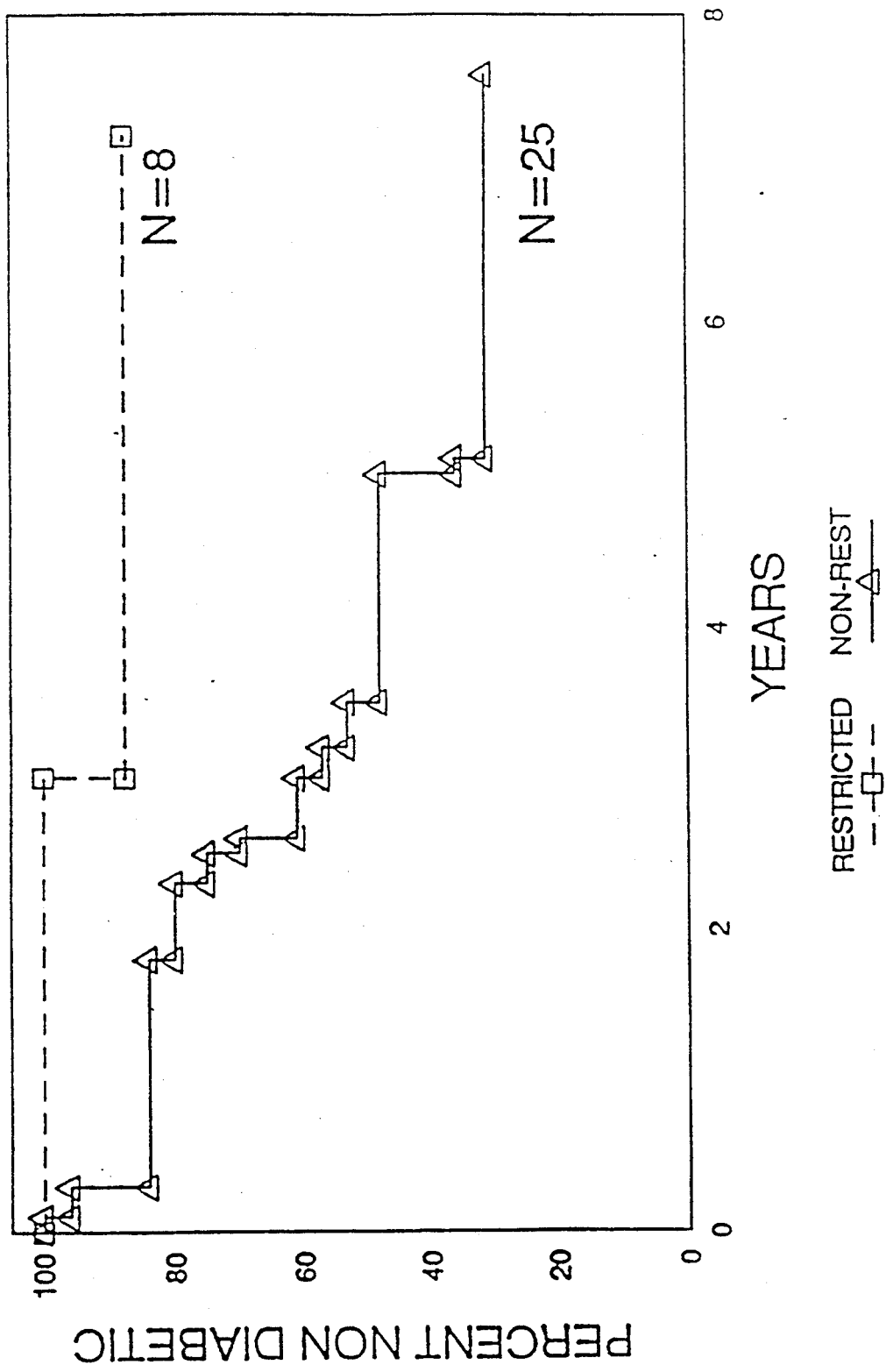

FIG. 6A FIG. 6B
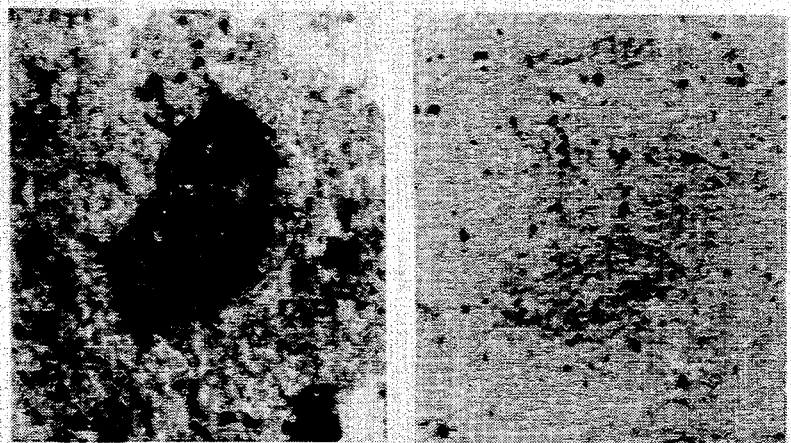
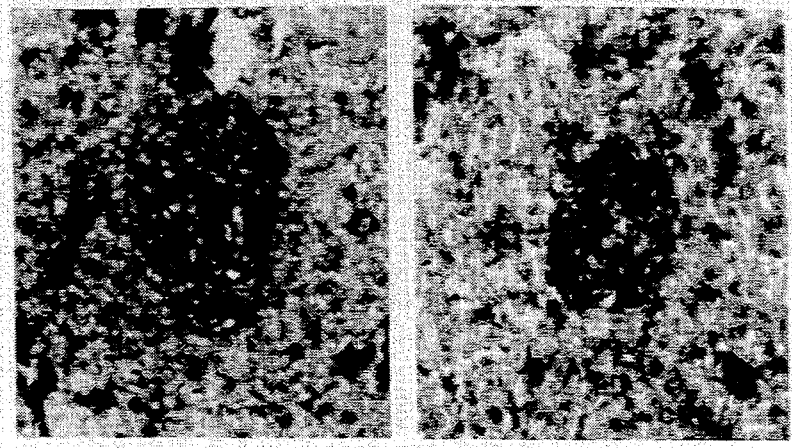
FIG. 6C FIG. 6D

METHOD OF ACCESSING THE RISKS OF DEVELOPING TYPE I DIABETES

GOVERNMENT SUPPORT

The work leading to this invention was supported, in part, by research grants from the United States government.

BACKGROUND OF THE INVENTION

Diabetes is a chronic, complex metabolic disease that results in the inability of the body to properly maintain and use carbohydrates, fats, and proteins. It results from the interaction of various hereditary and environmental factors and is characterized by high blood glucose levels caused by a deficiency in insulin production or an impairment of its utilization. Most cases of diabetes fall into two clinical types: insulin-dependent diabetes mellitus (IDD or type I diabetes) and non-insulin-dependent diabetes mellitus (NIDD). Each type has a different prognosis, treatment and cause.

In recent years our understanding of the pathophysiology of type I diabetes has increased such that type I diabetes is now generally considered to be a chronic autoimmune disease with a long prodromal phase (Castano et al. (1990) *Ann Rev Immunol* 8:647–679; Maclaren et al. (1988) *Diabetes* 37:591–594; Lernmark et al. (1989) *Clin Immunol Immunopath* 53:358–399). During this prodromal phase and at the onset of overt diabetes, one or more autoantibodies are usually present. Three abnormalities predictive of type I diabetes are cytoplasmic islet cell autoantibodies (ICA) in excess of 20 JDF units (Bonifacio et al. (1990) *Lancet* 335:147–149), insulin autoantibodies (IAA) detected with fluid phase radioassays in association with islet cell autoantibodies (Ziegler et al. (1989) *Diabetes* 38:1320–1325), and first phase insulin release less that than the first percentile during an intravenous glucose tolerance test (Vardi et al. (1991) *Diabetologia* 34:93–102).

Identification of the prediabetic state in diabetes is essential in efforts to prevent the development of the disease. Perhaps the single most important advance of the past two decades in diabetes research has been recognition that autoimmune destruction of beta cells takes months or years to reach completion, whereas currently the clinical diagnosis of diabetes is almost never made until the destructive process is nearly complete and insulin injections are required to prevent death. Intervention before the insulin-producing cells have been irreversibly destroyed can provide a strategy to prevent progression of diabetes and its complications.

Cytoplasmic ICA have been extensively evaluated for the prediction of the development of type I diabetes. They have been found to be a highly predictive marker, particularly if present in high titer (Riley et al. (1990) *N Engl J Med* 323:1167–1172; Ziegler et al. (1989) *Diabetes* 38:1320–1325) Nevertheless, in all reported studies of more than five years of prospective observation of ICA positive first degree relatives of type I diabetics, a significant number of relatives have not progressed to diabetes.

SUMMARY OF THE INVENTION

This invention pertains to a method for determining the risk of an individual who expresses Islet Cell Autoantibodies (ICA) of progressing to type I diabetes. The method comprises determining whether the ICA of the individual are either restricted or non-restricted, where individuals expressing non-restricted ICA are at a higher risk of developing type I diabetes than are individuals exhibiting restricted ICA and ICA negative individuals. There is a strong correlation between progression to type I diabetes and the expression of non-restricted ICA by an individual. In contrast, individuals expressing restricted ICA significantly less often progress to type I diabetes than do non-restricted ICA individuals.

Restricted ICA are different from non-restricted ICA in at least the following ways:

A. restricted ICA are essentially anti-GAD antibodies and can be completely absorbed by incubation with GAD, whereas non-restricted ICA are only partially, if at all, absorbed upon incubation with GAD.

B. restricted ICA react with beta-cells of human and rat islets, but not with mouse islets. Non-restricted ICA react with human, rat and mouse islets.

C. restricted ICA react in a Stiff-Man Syndrome-like fashion, including the ability to stain GABAergic neurons in brain sections and stain GAD in western blots of brain extracts. Non-restricted ICA do not react with brain sections, and rarely with GAD in western blots.

D. restricted ICA display a higher titer of anti-GAD antibodies than do non-restricted ICA.

These differences can be used as a basis to distinguish between restricted and non-restricted ICA and to assess the risk of an individual progressing to type I diabetes. In a preferred method, the reactivity of an individual's serum with human or rat islets is assessed wherein the serum is or is not pre-incubated with GAD. As in a standard test for ICA, human or rat islets (for example, a section of pancreas) are contacted with the samples under conditions which allow ICA in the sample to bind the islet cells. ICA binding (e.g. immunocytological staining) can be visualized by, for instance, immunofluorescence or enzyme-linked procedures, wherein a second antibody or antibody-binding agent, coupled with either a fluorescent compound or an enzyme respectively, is used. Staining of the islets by the serum which has not been preincubated with GAD indicates that the individual is ICA positive.

Analysis of the ability of the GAD preincubated sample to stain islets allows identification of the ICA subsets. If the individual expresses restricted ICA, preincubation with GAD antigen will substantially completely absorb the ICA and therefor eliminate the ability of the serum to stain the islet cells. On the other hand, preincubation with GAD does not significantly reduce the ability of non-restricted ICA to stain the islet cells. Individuals exhibiting non-restricted ICA are much more likely to progress to type I diabetes than are restricted ICA individuals or ICA-negative individuals.

BRIEF DESCRIPTION OF THE FIGURES

FIG. 3 shows the life table analysis of progression to diabetes of relatives with the restricted versus non-restricted pattern of ICA.

FIG. 5A is GAD6 monoclonal antibody; FIG. 5B is serum from a Stiff-Man Syndrome individual; FIG. 5C is restricted ICA and FIG. 5 is non-restricted ICA.

FIGS. 6A–6D show the effect of preincubation with purified porcine GAD on the reactivity of restricted ICA and non-restricted ICA with human pancreas sections. FIG. 6A is restricted ICA; FIG. 6B is restricted ICA preincubated with purified porcine GAD; FIG. 6C is non-restricted ICA and FIG. 6D is non-restricted ICA preincubated with purified porcine GAD.

DETAILED DESCRIPTION OF THE INVENTION

Figure 1A:
FIGS. 1A–1L show the immunoperoxidase staining of rat (FIGS. 1A–1C and FIGS. 1G–1I) and mouse (FIGS. 1D–1F and FIGS. 1J–1L) pancreas with sera diluted 1:5 (FIGS. 1A, 1D, 1G and 1J), 1:25 (FIGS. 1B, 1C, 1H and 1K) and 1:125 (FIGS. 1C, 1F, 1I and 1L). The relative (ptid 1271) with the restricted ICA pattern reacts strongly with rat pancreas (FIGS. 1G–1I) but is totally non-reactive at all dilutions with mouse pancreas (FIGS. 1J–1L) while the relative with the non-restricted ICA pattern (ptid 359) reacts equally well with mouse and rat pancreas FIGS. 1A–1C and FIGS. 1D–1F. Sera from both relatives react strongly with human pancreas (not shown).
Figure 1B:
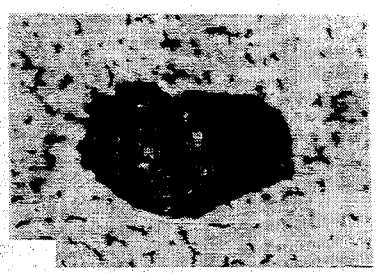
Figure 1C:
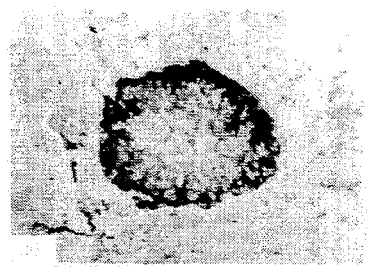
Figure 1D:
Figure 1E:
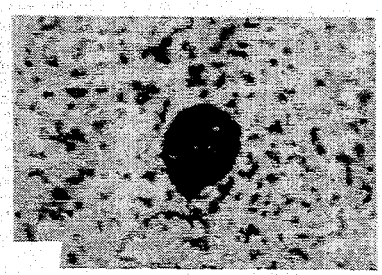
Figure 1F:
Figure 1G:
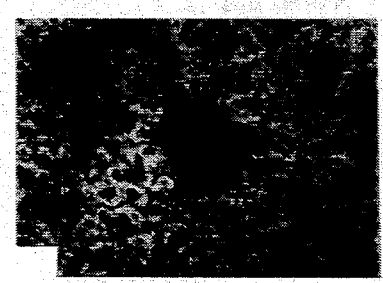
Figure 1H:
Figure 1I:
Figure 1J:
Figure 1K:
Figure 1L:
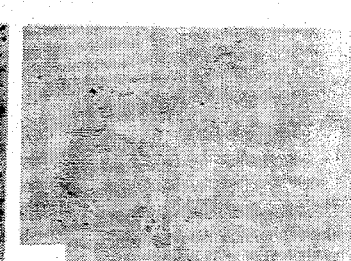
Figure 2A:
FIGS. 2A–2D show the contrasting cell reactivity of sera of the restricted (FIG. 2A) versus non-restricted (FIG. 2C) pattern. Serial sections were stained either with patients' sera or anti-glucagon antibodies (FIGS. 2B and 2D). Arrows outline the outer edge of the islets. Sera of the non-restricted (FIG. 2C) react with glucagon containing islet cells and beta cells, while sera of the restricted pattern fail to react with anti-glucagon reactive islet cells.
Figure 2B:
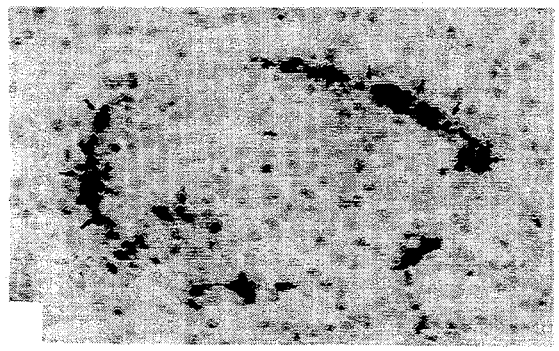
Figure 2C:
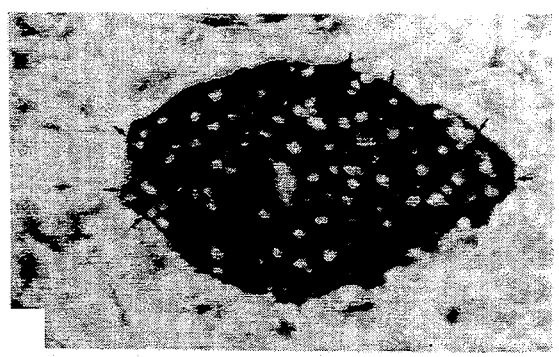
Figure 2D:
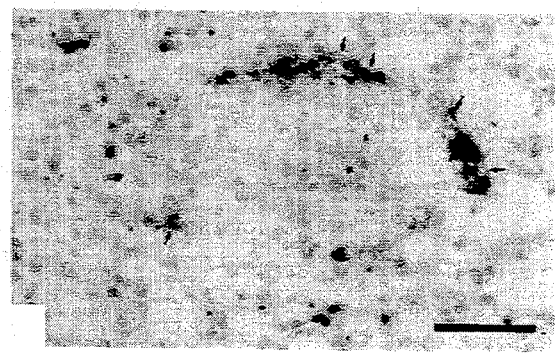

It has been discovered that a majority of ICA positive individuals who maintain normal phase insulin secretion upon long-term follow up studies, express an unusual form of ICA relative to those patients who have developed type I diabetes. In evaluating reactivity of ICA positive sera with human, rat and mouse pancreas, a subset of the ICA positive individuals expressed antibodies reactive only with human and rat islets. This pattern of reactivity with human and rat islets, but not mouse islets, was termed "restricted". In contrast, the ability of the ICA positive sera to react with human, rat and mouse islets was termed "non-restricted".

In addition to this species dependence, restricted and non-restricted ICA have been further characterized as follows:
1. Restricted ICA are essentially comprised of anti-GAD antibodies. Restricted ICA, but not non-restricted ICA, can be completely absorbed by incubation with affinity purified glutamic acid decarboxylase (GAD).
2. Restricted ICA react only with beta-cells of the islets and not with islet cells lacking the GAD antigen. Non-restricted ICA, on the other hand, react with whole islets, including glucagon-containing cells.
3. The titer of anti-GAD antibodies is higher in individuals expressing restricted ICA relative to individuals expressing non-restricted ICA.
4. Restricted ICA react in a "Stiff-Man Syndrome" like fashion with GAD antigen and is able to stain GABAergic neurons in brain sections and western blots of brain extracts. In contrast, the non-restricted ICA do not react with brain sections and rarely with brain extracts in western blot analysis.

The expression of non-restricted ICA correlates with progression to type I diabetes, indicating that these individuals are at much greater risk than are individuals expressing restricted ICA or individuals lacking ICA. Differentiation between restricted or non-restricted ICA allows for more accurate prognosis of the development of type I diabetes.

Several different procedures can be used to determine whether individuals who express ICA exhibit the restricted or non-restricted form. In a preferred embodiment, restricted ICA (which are essentially anti-GAD antibodies) are distinguished from non-restricted ICA by the ability of GAD to abrogate ICA reactivity with human or rat islets. A portion of a serum or plasma sample is pre-incubated with GAD under conditions such that the GAD complexes with anti-GAD antibody in the sample. Affinity purified GAD can be obtained from porcine brain using antibodies specific for GAD. As in a standard test for ICA, human or rat islets (for example, a section of pancreas) are contacted with the GAD-preincubated sample and untreated sample under conditions which allow ICA in the samples to bind the islet cells. ICA reactivity (immunocytological staining) can be visualized by, for instance, immunofluorescence or enzyme-linked procedures. Typically, a second antibody such as anti-(human IgG)antibodies or antibody-binding agents such as protein A, coupled with either a fluorescent (e.g. fluorescein or rhodamine) compound or an enzyme (e.g. peroxidase) respectively, is used. Staining of the islets by the sample which has not been preincubated with GAD indicates that the individual is ICA positive.

Analysis of the ability of the GAD-preincubated sample to stain islets allows identification of the ICA subsets. If the individual expresses restricted ICA, preincubation with GAD will substantially completely absorb the ICA and therefor eliminate the ability of the serum to stain the islet cells. On the other hand, preincubation with GAD does not significantly reduce the ability of non-restricted ICA to stain the islet cells. Individuals exhibiting non-restricted ICA are much more likely to progress to type I diabetes than are restricted ICA individuals or ICA-negative individuals.

In another embodiment of the invention, restricted ICA and non-restricted ICA can be differentiated by the titer of anti-GAD antibodies. As explained, restricted ICA are essentially only GAD-specific antibodies. The anti-GAD titer of restricted ICA is higher than the anti-GAD titer of non-restricted ICA, based upon immunoprecipitation assays and western blot analysis. The titer of anti-GAD antibodies can be determined by radioimmunoassays, ELISA or other appropriate assays in a blood sample (e.g. plasma or serum) of an individual already determined to be ICA positive, and compared to the range of measured titers of anti-GAD antibodies in individuals exhibiting non-restricted ICA who have developed type I diabetes. An anti-GAD titer within the range of that found for non-restricted ICA individuals is indicative of a higher risk of the ICA positive individual progressing to type I diabetes. Anti-GAD titer ranges can be established and refined with population studies involving ICA positive individuals.

In other embodiments of the invention, restricted ICA and non-restricted ICA can be distinguished by the differential staining of histological samples. For example, restricted ICA react with human and rat islets but do not react significantly with mouse islets. In an immunocytological assay, mouse and either rat or human islet cells can be contacted with the biological fluid (or dilutions thereof) of an ICA positive individual such that autoantibodies bind the islet cells. Visualization of bound ICA can be accomplished by subsequent staining of the cells by standard techniques. For example, bound antibody can be stained with fluorescently-labeled (e.g., fluoroscein-or rhodamine-labeled) or with immunoperoxidase-labeled anti-(human IgG) antibodies. Staining of human and rat but not mouse islet cells is indicative of the restricted class of ICA, while staining of all three species' islets is indicative of non-restricted ICA.

Restricted and non-restricted ICA reactivity can also be distinguished in immunocytological assays based upon the differential staining of alpha and beta islet cells. As explained above, restricted ICA react only with beta cells, while non-restricted ICA react with both alpha and beta cells. In this assay, rat or human islet cells can be contacted with the biological fluid of an ICA positive individual under conditions conducive for ICA binding to the cells. Visualization of bound ICA can be accomplished as described above. Alternatively, overlap staining can be used to enhance detection and localization of ICA. For instance, the cells are stained with antibodies directed to epitopes unique to alpha-cells such as glucagon, or antibodies directed to epitopes unique to beta cells such as the glucose transporter Glut2, or antibodies reactive with all islet cells. This islet cell reactive antibody can be directly coupled to a fluorescent label, or visualized by way of a second labeled antibody as described above. Determination of the reactive pattern of the ICA is made by visualizing the staining pattern. Staining of human and rat beta islet cells but not alpha cells by ICA is indicative of the restricted class of ICA, while staining of both cell types is indicative of non-restricted ICA.

As detailed above, the identification of ICA positive individuals as being either restricted or non-restricted allows for the enhanced prediction of progression to type I diabetes. The early and accurate detection of this potentially devastating disease would facilitate the administration of treatments which would not be effective during the later stages of the disease when irreversible damage is extensive.

The presence of a high titer of anti-GAD antibodies in restricted ICA individuals suggests a possible protective role for this autoantibody, perhaps in masking antigens or modulating an anti-idiotypic network of antibodies. Therefor, restricted ICA or a population of anti-GAD antibodies having the specificity of restricted ICA or GAD (or immunogenic portions thereof), may be administered to prevent progression to type I diabetes.

There appears to be a strong correlation between the presence of the DQ beta allele, DQB1*0602 and both the lack of progression to type I diabetes and the expression of restricted ICA. With regard to restricted ICA versus non-restricted ICA, substantially no non-restricted ICA individuals have the DQB1*0602 allele, whereas a significant portion of restricted ICA individuals have this allele. Within the restricted ICA population, there appears to be an even further decreased risk of development of type I diabetes in those individuals with the 0602 allele. The 0602 allele may be used in further diagnostic assessment of diabetic risk.

The invention is illustrated further by the following exemplification of, inter alia, the identification of restricted and non-restricted classes of ICA, the strong correlation between non-restricted ICA and progression to type I diabetes and the reactivity of restricted ICA as being predominantly anti-GAD.

EXEMPLIFICATION

Population Studied

The sera analyzed were obtained from perspective evaluation of first degree relatives (Bleich et al. (1990) *Diabetes Care* 13:111–118). All the individuals studied were first degree relatives of patients with type I diabetes and none of the relatives were diabetic when the serum was drawn. The sera samples tested had previously been found to have greater than 40 JDF units of ICA (by the method of SriKanta et al. (1985) *Diabetes* 34:300–305). As described previously, insulin autoantibodies (IAA) were found with a competitive radioimmunoassay (Vardi et al. (1991) *Diabetologia* 34:93–102) intravenous glucose tolerance test (IVGTT) were performed with the sum of the insulin concentrations one and three minutes after the end of glucose infusion (0.5 g/Kg glucose infused over three minutes) reported.

To date, 33 ICA positive subjects have been studied to define their ICA subclass; the mean age of the relatives when the first sample was drawn was 20.99 yrs ±5.74 (SEM). Seventeen patients were female, and 16 were male. Twenty one out of 33 (61%) of the relative were both ICA and IAA positive and 14 out of 33 (42%) have subsequently developed diabetes.

Materials and Methods

PANCREAS: Human pancreas was obtained from the National Disease Research Interchange (Philadelphia, PA). Pancreas was frozen immediately after removal and kept frozen at −70° C. until cryostat sections (4−5 μm) were produced. Rat pancreas was obtained from 6 week old Wistar-Furth rats. Pancreas was snap frozen in liquid nitrogen and stored at −70° C. Cryostat sections were placed on gelatin dichromate-coated slides. Pancreas was obtained from C3H/HeJ mice (12−16 weeks old) and stored as described for the rat pancreas.

Affinity purified GAD was obtained by affinity purification of extracts of porcine brain using the GAD6 monoclonal antibody. GAD6 monoclonal antibody reacts specifically with the 65 kd form of GAD.

Murine IgM anti-islet cell monoclonal antibody A2B5 was used for double staining of rat sections. This monoclonal antibody binds to all islet-cells of chicken, mouse, rat and human pancreas. For the staining of alpha cells, a rabbit anti-porcine glucagon antibody was used, while the staining of beta cells was accomplished using a rabbit anti-rat glucose transporter antibody (glut2) was used.

Cytoplasmic islet cell antibodies (ICA) on human, rat and mouse pancreas were detected with the indirect immunoperoxidase method. The human, rat and mouse frozen sections were air-dried at room temperature for 5 minutes: the rat and mouse sections were subsequently acetone fixed for 5 minutes while human sections (as per standard ICA techniques) were not acetone fixed. The sections were then incubated with patient sera for 30 minutes at room temperature at several concentrations (undiluted, 1:5, 1:25, 1:125) diluted in Tris pH 7.4 buffer with 6 g trizma base (Trizma Base-Sigma, St. Louis, Mo.) and 5.8 g NaCl in 1 liter of distilled water containing 1% BSA (bovine serum albumin Sigma, St. Louis Mo.). After washing, the sections were incubated with anti-(human IgG) antibody-peroxidase conjugate and subsequently developed with a 0.05% diaminobenzidine solution (Diaminobenzidine-Sigma St. Louis, Mo.) plus 0.033% of hydrogen peroxide. The sections were subsequently mounted with AFT mounting medium (Behring, LaJolla, Calif.) and observed with a light microscope.

Two different methods were used to "double stain" tissue sections. In order to rapidly screen patient's sera for islet cell specificity of their antibodies, frozen rat sections were air dried, acetone fixed and then incubated for 30 minutes at room temperature with diluted patient sera. The monoclonal antibody A2B5 was added to the patient sera at a final concentration of 1:100 (diluted in Tris BSA 1%) and incubated for an additional 30 minutes. After washing with tris buffer, fluorescein conjugated goat anti-human IgG (Cappel Laboratories, Cochranville, Pa.) diluted 1:20 in Tris buffer containing 1% bovine serum albumin was added and incubated for 30 minutes. The sections were washed and a rhodamine conjugated goat anti-mouse IgM antibody (Dako, Santa Barbara, Calif.) diluted 1:100 in BSA plus 5% normal rabbit serum was added and incubated for 30 minutes. Following washing with Tris buffer the sections were mounted in AFT mounting medium and examined with a Leitz Dialux fluorescence microscope with either a fluorescein or a rhodamine filter. Sera were also analyzed for beta cell specificity of their antibodies using a rabbit antibody to the rat glucose transporter (glut2). Patient's serum was added to the rat sections and the glut2 antibody was added after 30 minutes without washing. After a subsequent 30 minute incubation, the sections were washed and the fluoresceinated anti-human IgG previously described was incubated with the sections. After washing, a rhodaminated goat anti-rabbit anti-sera was added to the section (Cappel Laboratories, Cochranville, Pa.) diluted 1:100 in Tris buffer with 1% bovine serum albumin plus 1% normal human sera. The sections were washed, mounted and examined as previously described. Glut2 is expressed only by beta cells and thus sera which reacted only with Glut2 expressing cells are beta cell specific.

As a final evaluation of the pattern of staining of the sera, we studied serial cryostat sections of Wistar-Furth rat pancreas. Four serial sections were obtained for each analysis: the first and the last were stained with a rabbit anti-glucagon antibody, while the second and the third were stained with patient sera (immunoperoxidase protein-A technique). The anti-glucagon immunocytochemical localization used the peroxidase anti-peroxidase method of Sternberger (Sternberger *Immunocytochemistry*, Prentice Hall, Inc.:New Jersey 1974).

MHC TYPING: DNA typing with oligonucleotide probes was performed for DQ Beta alleles utilizing reagents and the protocol of the 11th International Histocompatibility Workshop. For 11 relatives, class II DNA typing (reverse dot blot) was also performed. In brief, 0.5 μg of genomic DNA from each subject was amplified by the polymerase chain reaction (PCR) with DQ$\beta$ specific primers and the PCR product was then dot blotted onto a nylon membrane. Membranes were then hybridized with 32 P labelled oligonucleotide probes (SSO) and in turn exposed to Kodak-X-OMAT-R film at $-80°$ C. for 2 to 4 h for autoradiography.

Fisher's exact test and linear regression were utilized for statistical analysis.

Results

In evaluating reactivity of ICA positive sera with human, rat and mouse pancreas, a subset of relatives expressed antibodies reactive only with human and rat islets.

FIGS. 1A–1L illustrate the reactivity of two high titer ICA positive sera with rat (FIGS. 1D–1L) and mouse (FIGS. 1D–1F and 1J–1L) pancreas (both sera are complement fixing ICA positive on human pancreas and $>640$ JDF units). Serum 1 (FIGS. 1A–1F) reacts with both rat and mouse pancreas at all dilutions shown (1:5, 1:25 and 1:125). In contrast serum 2 despite showing equally strong reactivity with rat and human pancreas fail to react with mouse islets, at all dilutions shown (and also when evaluated undiluted, not shown). This pattern of reactivity with human and rat islets, but not with mouse islets we have termed "restricted." Amongst 33 ICA positive sera studied, 8 (25%) were found to have a "restricted" pattern of reactivity; these sera failed to react at all dilutions with C3H/HeJ mouse pancreas while reacting with WF rat and human pancreas. Two of these sera were positive on rat pancreas at a dilution of 1:625, another was positive to 1:125, four to dilutions of 1:25, and one to a dilution of 1:4. The remaining twenty-five sera reacted with mouse as well with rat pancreas and the end point dilution of the sera on the two tissues were highly correlated (r+0.75 p<.01).

In addition to the species pattern of reactivity of ICA positive individuals, it can be demonstrated by immunoperoxidase staining of rat pancreas that sera of the restricted ICA pattern frequently stained fewer cells within the islets (and predominantly cells within the center of islets) while sera of the non-restricted ICA pattern reacted with all islet cells and particularly well with cells at the periphery of the islets (alpha-cells). The staining patterns of the two classes of sera were therefore studied on rat pancreas utilizing three different methods for evaluating cell specificity. The sera staining pattern was evaluated on serial sections with an antibody reacting with alpha cells and analyzed by planimetry. Restricted ICA did not react with glucagon containing cells while non-restricted ICA reacted with the whole islet including the glucagon containing cells (FIGS. 2A–2D). In a similar fashion there was complete overlap of staining with rabbit antibody to the glucose transporter Glut2 which is beta cell specific and sera of the restricted ICA pattern (not shown). Finally, to rapidly screen ICA positive sera for their islet cell reactivity pattern, rat pancreas was double stained with monoclonal antibody A2B5 which reacts with all islet cells. All the sera with restricted species reactivity studied (4/4) reacted only with a subset of A2B5 positive cells while all the non-restricted or class I sera examined with this system (5/5) reacted with all A2B5 positive cells.

The beta cell specificity of the reactivity of the cytoplasmic ICA suggested that the antigen recognized might be GAD, since GAD is specifically expressed by beta cells within islets. Patients with Stiff-man Syndrome with anti-GAD antibodies, but not most new onset diabetics with anti-GAD antibodies (anti-64K) are able to stain tissue sections, including brain sections and islets. FIGS. 5A–5D illustrate the staining of rat brain by restricted ICA and non-restricted ICA. Reactivity of sera from a patient with Stiff-man Syndrome and monoclonal antibody GAD6 is also shown. The restricted ICA and the Stiff-man Syndrome sera stained rat islets, but not mouse islets (not shown) and reacted with brain sections in an anti-GAD pattern. In contrast, the non-restricted ICA reacted with both mouse and rat islets (not shown), but not brain. Thus, the restricted ICA, but not non-restricted ICA had antibodies with a pattern similar to anti-GAD antibodies of a patient with "Stiff-man Syndrome" and a monoclonal anti-GAD antibody.

To define whether all the autoantibodies of the restricted ICA detected by staining sections of human pancreas could be absorbed with affinity purified GAD and whether in contrast, the antibodies of the non-restricted ICA fail to react with GAD, both sera were incubated with affinity purified GAD (FIGS. 6A–6D). Immunocytological staining with ICA positive sera results in staining of islets by both restricted and non-restricted ICA (visualized by indirect immunoperoxidase staining). However, preincubation with GAD entirely abrogates staining of islets by restricted ICA while not significantly altering the staining of islets by non-restricted ICA. To date 3/3 sera with the restricted pattern have been totally absorbed by incubation with affinity purified GAD, while none of 5 sera with non-restricted ICA were affected by incubation with GAD.

To assess the prognostic significance of the described ICA patterns, ICA positive relatives were subdivided by ICA class and analyzed for age, expression of insulin autoantibodies, length of follow up, and progression to diabetes (Table 1). Relatives with the restricted ICA pattern were on average older than relatives with the non-restricted pattern (mean age 37.27±4.09 versus 15.78±4.41, $p<0.05$). Nevertheless, two ICA positive relatives with a non-restricted ICA pattern developed diabetes after age 30 (ptid 2316,6573). Such overlap in age suggests that the pattern of ICA is predictive of progression to diabetes despite older age.

Figure 4A:
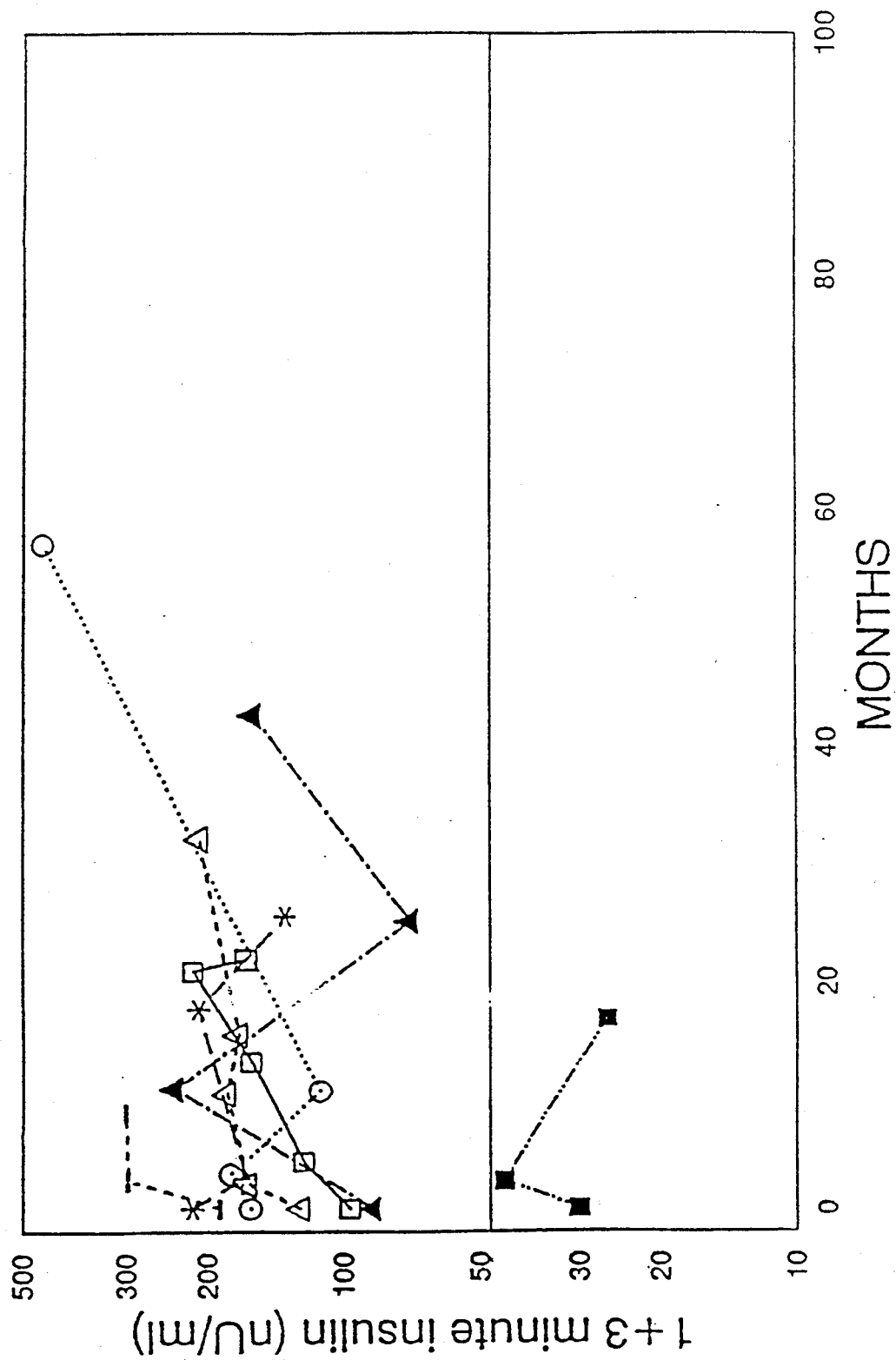
FIG. 4A shows the sequential intravenous glucose tolerance testing in ICA positive relatives with restricted ICA. Only one relative had first phase insulin secretion (sum of 1+3 minute insulin post intravenous glucose shown on the Y axis) less than 48 uU/ml (dashed horizontal lines) Y axis is on a 10-g scale.
Figure 4B:
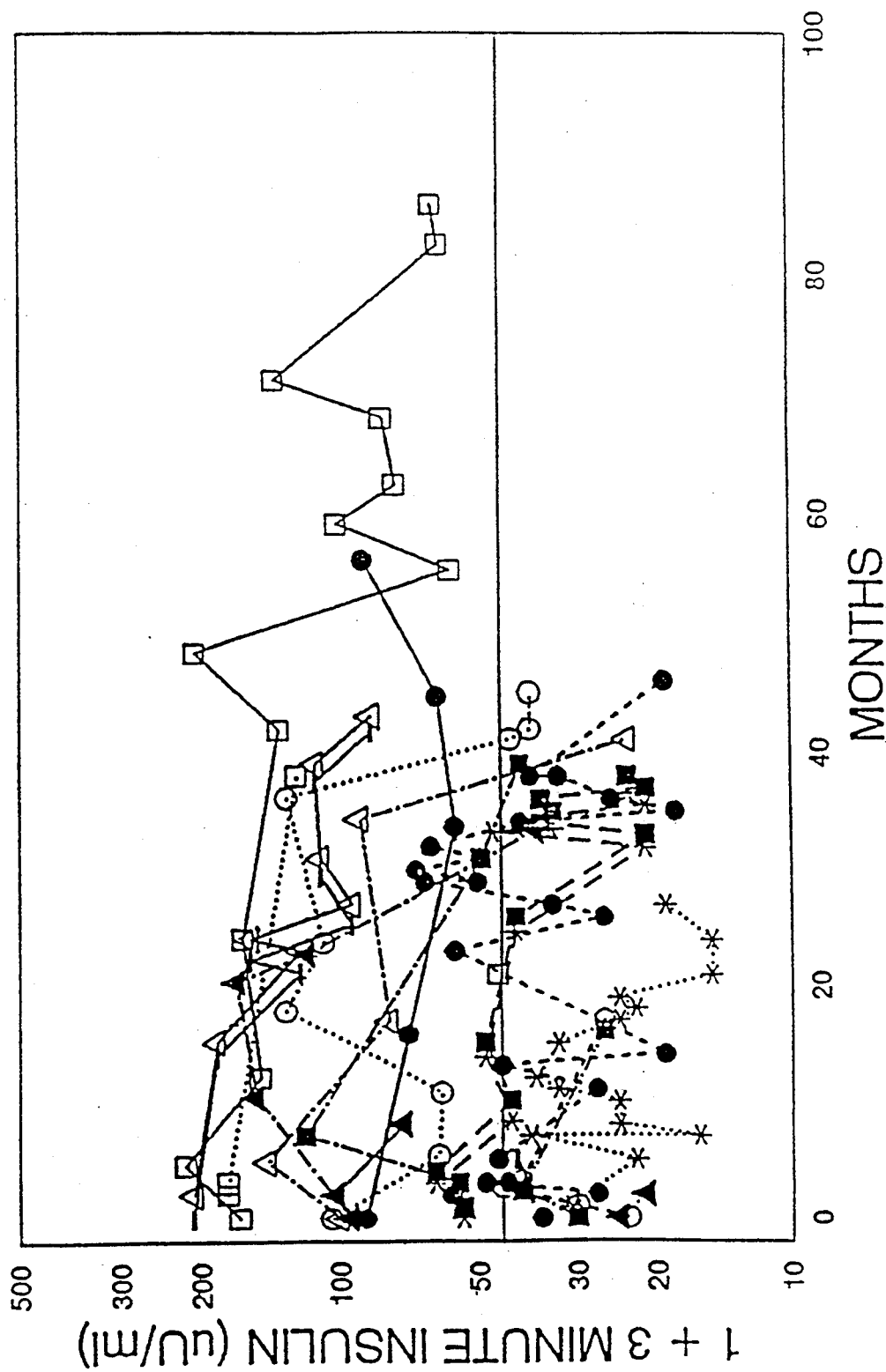
FIG. 4B shows the sequential intravenous glucose tolerance testing in ICA positive relatives with non-restricted ICA. Most at first measurement or on follow-up have an IVGTT below 48 uU/mL (horizontal line) in contrast to relatives with restricted ICA.
Figure 5A:
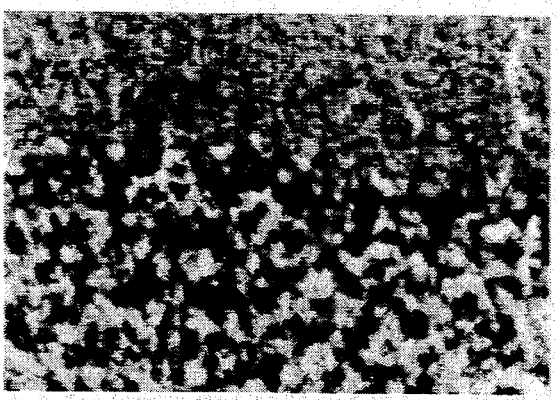
FIGS. 5A–5D show the reactivity of antibodies with rat brain.
Figure 5B:
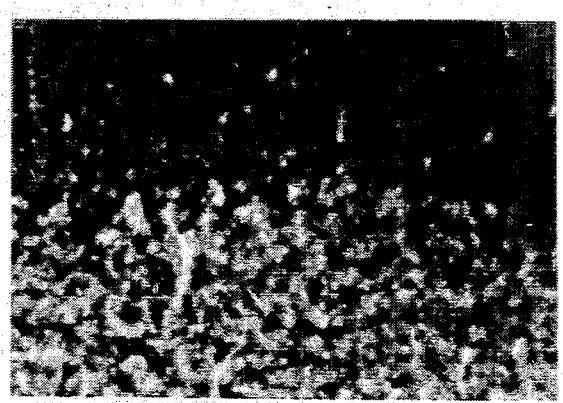
Figure 5C:
Figure 5D:

FIG. 3 illustrates life table analysis of progression to diabetes of relatives with the restricted versus non-restricted pattern of ICA. Only one of the relatives with the restricted ICA pattern has progressed to diabetes. In contrast, by five years of follow up 52% (13/25) of relatives with the non-restricted pattern have progressed to diabetes. Only five of the 25 (25%) relatives with non-restricted ICA have been followed for more than 4 years without developing diabetes and one of these five has an IVGTT response below the 1st percentile of normal (below 50 nu/ml) (ptid 3687). In contrast, despite high titers of ICA, only one of the relatives with the restricted ICA pattern (mean follow up 3.6 years) became diabetic and none of the remaining seven relatives with restricted ICA had an IVGTT below the first percentile (FIGS. 4A–4B) (⅛ compared to 13/25,

TABLE 1

RELATIVES WITH RESTRICTED (R) AND NON-RESTRICTED ICA (N)

| Relative ID NO | AGE[1] | ICA[2] | CIAA[3] | Years To Diabetes[4] | Years[4] Follow-up | Initial IVGTT[5] | Last IVGTT[5] |
|---|---|---|---|---|---|---|---|
| 10791 N | 2.5 | 640 | 95* | | 0.5 | 26* | |
| 8974 N | 6.4 | 320 | 433* | | 4.2 | 56 | 53 |
| 10493 N | 7 | 160 | 142* | | 1.2 | 95 | 38* |
| 3901 N | 8 | 160 | 493* | | 2.6 | 22* | 36* |
| 1450 N | 8.2 | 320 | 221* | 1.4 | | 29* | |
| 5097 N | 8.7 | 320 | 150* | | 3.2 | 55 | 40* |
| 1840 N | 8.8 | 640 | 24 | | 5.5 | 101 | 68 |
| 5582 N | 9 | POS | 193* | 2.1 | | 31* | 19* |
| 2279 N | 9.5 | 40 | 54* | 3.2 | | 54 | 23* |
| 4244 N | 9.8 | POS | 351* | 0.2 | | 57 | |
| 360 N | 10 | 80 | 54* | 5.1 | | 100 | 23* |
| 6056 N | 10.3 | 320 | 391* | 0.3 | | | |
| 533 N | 11 | 80 | 268* | 2.6 | | 45* | |
| 2054 N | 11.2 | 160 | 179* | 1.9 | | 21* | |
| 4147 N | 11.8 | 640 | 208* | | 4.5 | 207 | 85 |
| 3687 N | 12.2 | 320 | 159* | | 5.8 | 71 | 33* |
| 1230 N | 13.1 | 20 | 248* | 2.9 | 2.9 | 60 | 83 |
| 1852 N | 14.2 | 640 | 282* | | 3.6 | 104 | 38* |
| 359 N | 14.6 | 1280 | 96* | | 7.6 | 150 | 72 |
| 3626 N | 17 | 320 | 56* | 5.1 | | 151 | 37* |
| 11071 N | 20 | 640 | 122* | | 0.3 | 95 | 139 |
| 2201 N | 29.2 | POS | 16 | 3.5 | | 98 | 21* |
| 5136 N | 30 | 640 | 57* | 5 | | 174 | 123 |
| 6573 N | 38 | 320 | 25 | 0.4 | | 38* | 41* |
| 2316 N | 58 | POS | 29 | 2.5 | | 25* | 24* |
| 9824 R*** | 10.8 | 320 | 18 | | 0.4 | 185 | |
| 726 R | 12.5 | 160 | 463* | | 6.2 | 97 | 210 |
| 4550 R | 20 | 320 | 18 | | 2.6 | 215 | 134 |
| 3401 R | 42 | 640 | 10 | | 3.7 | 86 | 158 |
| 1271 R | 42.6 | 640 | 20 | | 4.0 | 124 | 207 |
| 5476 R | 50 | 640 | 29 | | 4.3 | 186 | 296 |
| 2204 R | 54.5 | 640 | 25 | | 7.8 | 161 | 154 |
| 3440 R | 65.8 | POS | 35 | 3.2 | | 23* | 26* |

[1] Age when sera obtained (yrs)
[2] ICA: Cytoplasmic islet cell antibodies expressed in JDF units or if end point titer not available indicated as pos for positive.
[3] CIAA: competitive insulin autoantibodies expressed in nanounits/ml of insulin specifically precipated (assayed in the presence and absence of unlabeled insulin) as previously described (normal <39 nU/ml).
[4] Years from the first encounter with the relative to overt diabetes or continuing non-diabetic follow-up.
[5] Sum of insulin concentrations expressed in uU/ml (one plus three minutes) following infusion of intravenous glucose (first percentile of normal = 48 uU/ml).
*First phase insulin secretion less than 48 uU/ml or insulin autoantibodies >39 Nu/ml.
**N = non-restricted ICA.
***R = restricted ICA.

p=<0.05). Concordant with the lack of progression to type I diabetes, only ⅛ of the relatives with restricted ICA (despite ICA beta cell specificity) have insulin autoantibodies exceeding 39 nu/ml while 20/25 relatives with non-restricted ICA have insulin autoantibodies exceeding our normal range (P<.001).

DNA typing for DQ beta alleles has been performed for 5 out of 8 relatives with restricted ICA and for 8 out 25 relatives with non-restricted ICA. Four of 5 (80%) relatives with restricted ICA had the DQB1*0602 allele versus 0 out of 8 non restricted ICA positive relatives (p=.006). The association of restricted ICA with DQB1*0602 suggests that perhaps the DQB1*0602 allele can be used in an assay to differentiate between restricted and non-restricted ICA. In addition, the exaggerated immune response to GAD may protect from diabetes in otherwise susceptible individuals.

Equivalents

Those skilled in the art will recognize, or be able to ascertain using no more than routine experimentation, numerous equivalents to the specific procedures described herein. Such equivalents are considered to be within the scope of this invention and are covered by the following claims.

We claim:

1. A method of determining the risk of an individual who expresses Islet Cell Autoantibodies (ICA) of progressing to type I diabetes, comprising:
    a. obtaining a blood sample from the individual;
    b. preincubating the sample with purified glutamic acid decarboxylase (GAD) of the 65 kd form under conditions such that the GAD can form complexes with anti-GAD antibodies in the sample;
    c. contacting the GAD-preincubated sample with human or rat islet cells under conditions which allow uncomplexed ICA in the sample to bind to the cells; and determining the extent of ICA binding to the cells, wherein substantially complete elimination of ICA binding to the cells resulting from 65 kd GSD preincubation indicates that the individual has restricted ICA and the lack of substantially complete elimination of ICA binding to the cells resulting from 65 kd GAD preinccubation indicates that the individual has non-restricted ICA and a higher risk of developing type I diabetes.

2. The method of claim 1, wherein the blood sample is serum or plasma.

3. The method of claim 1, wherein the ICA binding is determined by immunocytological staining.

4. The method for determining the risk of an individual who expresses Islet Cell Autoantibodies (ICA) of progressing to type I diabetes, comprising:
    identifying ICA of the individual as restricted or non-restricted, wherein an individual expressing non-restricted ICA is at a higher risk of developing type I diabetes than an individual expressing restricted ICA.

5. The method of claim 4, wherein ICA are identified as restricted or non-restricted by contacting the ICA of the individual with purified glutamic acid decarboxylase of the 65 kd form (GAD) and determining whether the ICA are substantially completely absorbed by said GAD, wherein substantially complete absorption by said GAD indicates that the individual has restricted ICA and the lack of substantially complete absorption by said GAD indicates that the individual has non-restricted ICA.

6. The method of claim 4 wherein. ICA of the individual are identified as restricted or non-restricted by contacting the ICA with human or rat beta islet cells and mouse beta islet cells and determining whether the ICA react with human or rat beta islet cells and mouse beta islet cells, wherein restricted ICA react with human and rat beta islet cells but not mouse beta islet cells and non-restricted ICA reacts with human, rat and mouse beta islet cells.

7. The method of claim 5, further comprising contacting the ICA with human or rat beta islet cells and mouse beta islet cells and determining whether the ICA react with human or rat beta islet cells and mouse beta islet cells, wherein restricted ICA react with human and rat beta islet cells but not mouse beta islet cells and non-restricted ICA react with human, rat and mouse beta islet cells.

* * * * *